Figure 1:
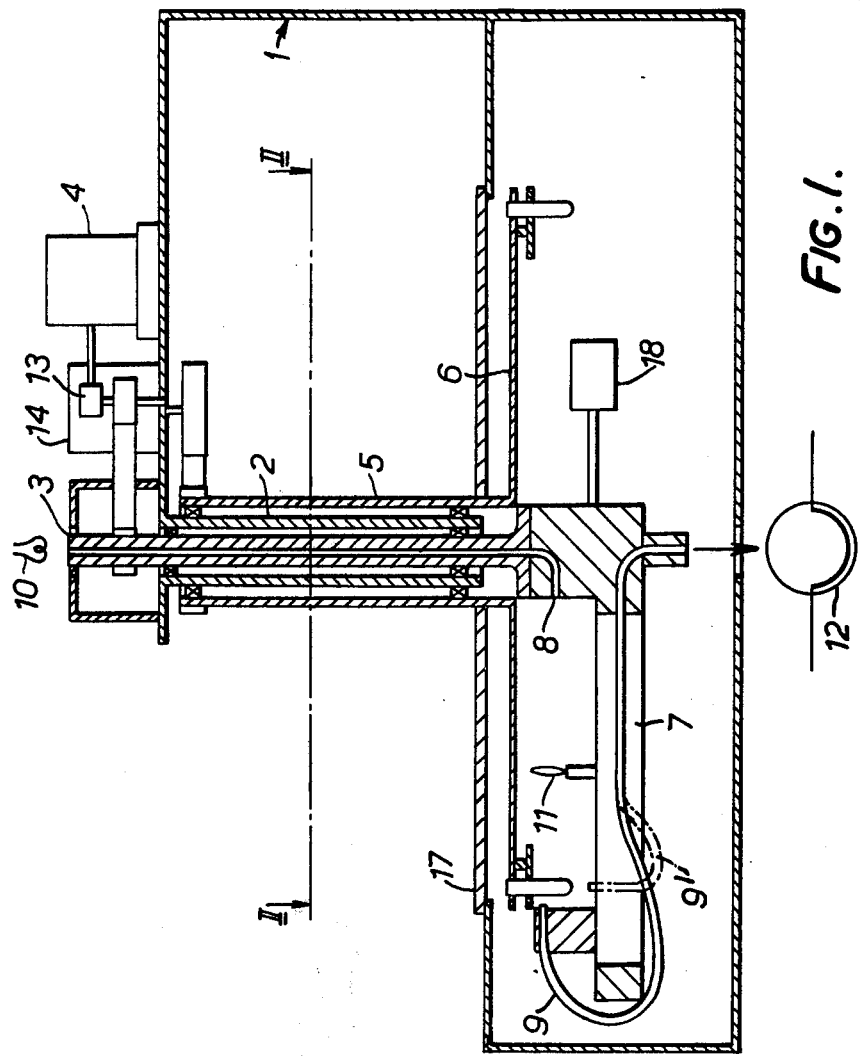

United States Patent [19]

Greaves et al.

[11] 4,007,011
[45] Feb. 8, 1977

[54] SPECIMEN TREATMENT APPARATUS

[75] Inventors: Geoffrey Stuart Greaves; Roger Abraham Bunce, both of Birmingham, England

[73] Assignee: The Secretary of State for Social Services in Her Britannic Majesty's Government of the United Kingdom of Great Britain and Northern Ireland, London, England

[22] Filed: Apr. 29, 1975

[21] Appl. No.: 572,716

[30] Foreign Application Priority Data

May 8, 1974 United Kingdom ............ 20389/74

[52] U.S. Cl. .............................. 23/259; 23/253 R; 259/13
[51] Int. Cl.² .................. B01F 11/00; G01N 21/00
[58] Field of Search .......... 23/253 R, 259; 259/13, 259/54–57, 73, 75; 233/3, 5

[56] References Cited

UNITED STATES PATENTS

| | | | |
|---|---|---|---|
| 3,617,222 | 11/1971 | Matte | 23/230 R |
| 3,623,844 | 11/1971 | Anthon | 23/259 X |
| 3,787,185 | 1/1974 | Rohrbaugh et al. | 23/253 R |
| 3,838,809 | 10/1974 | Williams | 23/259 X |
| 3,876,379 | 4/1975 | Ghim | 23/259 |

FOREIGN PATENTS OR APPLICATIONS 637,183  12/1963  Belgium ........................... 259/13

*Primary Examiner*—Morris O. Wolk
*Assistant Examiner*—Timothy W. Hagan
*Attorney, Agent, or Firm*—Reed Smith Shaw and McClay

[57] ABSTRACT

Specimen agitation apparatus comprises a horizontal turntable carrying, around its periphery, a plurality of substantially equally spaced vessels for receiving specimens to be agitated. The turntable is rotated stepwise about its central axis by a stepping motor which applies driving impulses to the turntable so as to cause it to rotate from a first rotational position to a second rotational position, but before coming to rest at the second position the turntable oscillates about the central axis to agitate the specimens.

10 Claims, 3 Drawing Figures

SPECIMEN TREATMENT APPARATUS

This invention relates to specimen agitation apparatus.

According to the present invention there is provided specimen agitation apparatus comprising a turntable mounted to rotate about a central axis and formed to carry, at respective positions substantially equally spaced from the said central axis and distributed substantially uniformly about the said central axis, a plurality of vessels for receiving liquid specimens to be agitated, and stepping drive means connected to the turntable to bring about stepwise rotation thereof about the said central axis when the apparatus is in use, the stepping drive means being arranged to apply driving impulses to the turntable to bring about rotation thereof, and the stepping drive means and the turntable being so arranged that when the turntable is in a first rotational position about the said central axis and a driving impulse is applied to the turntable by the stepping drive means the turntable rotates to a second rotational position about the said central axis but before coming to rest at the second rotational position oscillates about the said central axis.

Figure 2:
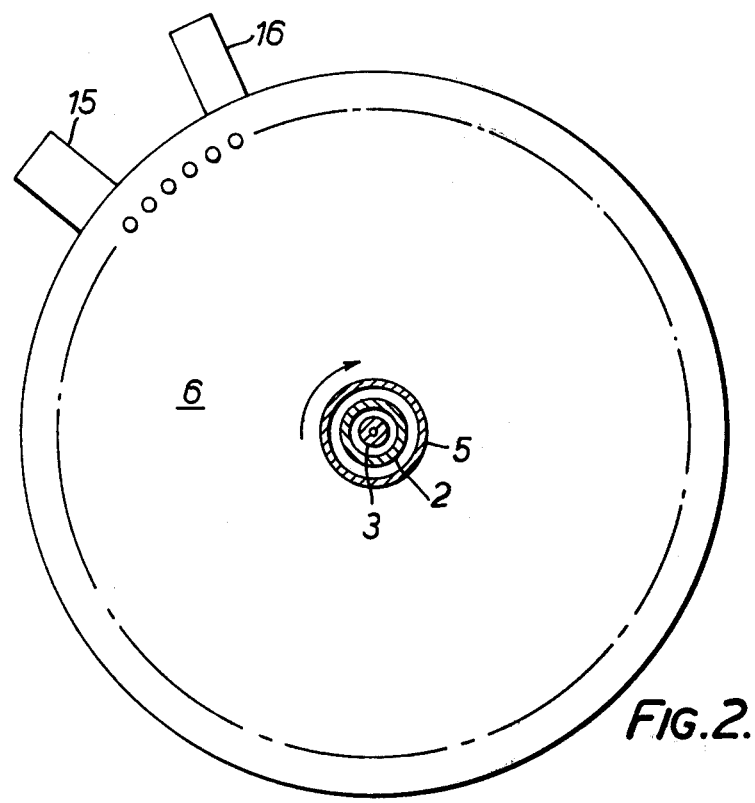
Figure 3:
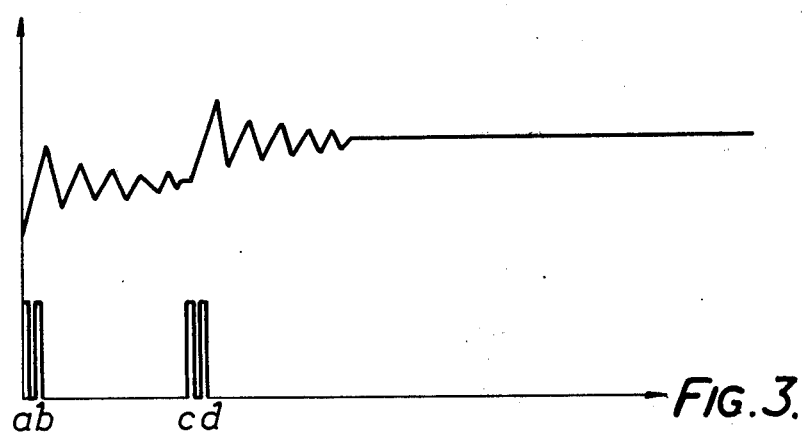

For a better understanding of the invention and to show how the same may be carried into effect, reference will now be made, by way of example, to the accompanying drawings, in which:

FIG. 1 shows a vertical sectional view of specimen agitation apparatus forming part of an automatic blood analysing machine, FIG. 2 shows a horizontal sectional view of the apparatus, taken on the section line marked II—II in FIG. 1, and FIG. 3 shows a graph.

The machine illustrated is used for colorimetric, light scattering and fluorimetric evaluation of reactions between samples of blood and reagent(s), and comprises a stationary frame 1 which carries a hollow vertical trunnion 2. Extending coaxially inside the trunnion 2 is a hollow rotatable shaft 3 which is connected at its upper end by a pulley and belt arrangement and a gearbox 13 to an electric motor 4 mounted on the frame 1. The trunnion 2 is surrounded coaxially by a further rotatable shaft 5 which carries a horizontal carrier or table 6 at its lower end and is connected at its upper end by a further pulley and belt arrangement to a second electric motor 14, which is a stepping motor. The table 6, which is covered by a stationary cover 17, is circular, its centre being on the common axis of the trunnion 2 and the shafts 3 and 5, and has about its periphery a plurality of equally spaced cuvettes or vials. Most desirably, these vials are fixed relative to the table 6 but they may alternatively be removably fitted into notches in the table. Each vial extends downwardly from the level of the table into the interior of the frame 1. The shaft 3 is connected at its lower end, which is below the table 6, to a horizontal arm 7 which extends radially with respect to the shaft 3. The shaft 3 is also connected to a counterbalance 18 for the arm 7. The arm 7 carries two fiber optic light guides 8 and 9. The light guide 8 has an input end at the upper end of the shaft 3 and extends vertically downwards, coaxially within the shaft 3. At the lower end of the shaft 3 the guide 8 extends therefrom radially outwardly along the arm 7 and has an output end at a position along the arm which is inward of the periphery of the table 6. The output end of the guide 8 defines a slit-form output aperture. The guide 9 has an input end which is mounted on the arm 7 outward of the periphery of the table and aligned with the end of the guide 8. The input end of the guide 9 defines a slit-form input aperture. The guide 9 extends from the periphery of the table radially inwards along the arm 7 and has an output end which is directed vertically downwards along the axis of the shaft 3. The light guides are looped between their radial and axial portions in order to avoid imposing excessive curvature on the guides.

About the upper end of the shaft 3 is a lamp 10 arranged to direct light vertically downwards into a circular input aperture defined by the input end of the light guide 8. Between the lamp 10 and the input aperture may be mounted a filter or grating unit for selecting the wavelength of light entering the input aperture and thereby enabling different reactions to be evaluated. Radially outwardly of the output end of the guide 8 is an optical system comprising a correction slit (not shown), converging lens 11 and a further correction slit (not shown), for focusing light delivered by the guide 8 on liquid in a vial. The optical system is clamped to a horizontal slideway, formed in the arm 7, to facilitate adjustment. Light which is transmitted by the liquid is received by the guide 9 at its input end and is delivered to its output end from which it is directed vetically downwards, along the axis of the shaft 3, to a photomultiplier 12.

When the blood analysing machine is in operation, the table 6 is rotated stepwise by the motor 14 past a cleaning station 15, whereat the cuvettes mounted in the notches about the periphery of the table 6 are cleaned in situ, and dispensing means 16 (such as a dispensing station), whereat a sample of blood and a quantity of reagent (and possibly also diluent and/or dye) is placed in a different vial during each dwell period of the table 6 between successive stepwise rotational advancements of the table. At the same time, the motor 4 is caused to rotate the shaft 3 through at least one revolution during each dwell period, thus causing the arm 7 to rotate so that the light beam from the light guide 9 scans the vials in succession and the light transmitted by the liquids in the vials is received by the light guide 9 and passed to the photomultiplier 12 which provides an output voltage, the magnitude of which depends upon the intensity of light received by the guide 9. The photomultiplier 12 is connected to a computer (not shown) which stores a set of data for each revolution of the shaft 3, representing the output voltage of the photomultiplier 12 for each of the vials. When the shaft 3 is rotated at least twice during each dwell period, the computer uses the several sets of data to form a mean value for the output voltage of the photomultiplier in respect of each vial. In practice, it is more convenient to rotate the motor 4 continuously rather than for it to rotate only during each dwell period of the table 6. Then, the computer is arranged so as to disregard the data received during each stepwise rotational advancement of the table 6 between successive dwell periods. Furthermore, the computer 4 is so arranged that if during each dwell period the shaft 3 rotates through a non-integral number of revolutions, the computer accepts data only for the nearest integral number of revolutions of the shaft, below the actual number of revolutions undergone.

The machine operates continuously, i.e. when a sample has been placed in a given vial the table rotates until that vial reaches the cleaning station whereat the vial is cleaned and the vial passes from there to the dispensing means whereat another sample is placed therein, and so on, and the shaft 3 is rotated continuously so whilst a vial is passing from the dispensing means to the cleaning station it is scanned several times by the light beam from the light guide, and the computer uses the several sets of data to form a mean value for the output voltage of the photomultiplier in respect of each vial.

In the circumstances, therefore, the illustrated machine is used for colorimetric analysis of the blood samples. By making a slight modification, however, the machine may be used for light scattering or fluorimetric analysis of the blood samples. The modification is shown in broken lines in FIG. 1 and entails replacing the light guide 9 by a guide 9' whose input end is vertically below the vial and perpendicular to the output end of the guide 8 and placing a colour filter between the output end of the light guide 9' and the photomultiplier 12. Then the output voltage of the photomultiplier depends upon the intensity with which light from the guide 8 in a selected wavelength band, predetermined by the filter, leaves the vial.

In FIG. 2 of the drawings filed in connection with Great Britain Patent application No. 51988/73 and its divisional application No. 46608/74, a further modification is shown which enables the intensity of light collected from the vials in each of several different wavelength bands to be determined in the manner described in those applications.

As mentioned above, the motor 14 is a stepping motor which causes the table 6 to rotate stepwise in one sense about the common axis of the trunnion 2 and the shaft 3 and 5. The table remains stationary for a predetermined dwell time between successive steps whilst the vial at the cleaning station is cleaned and a sample of blood and a reagent are dispensed into the vial at the dispensing station. Each rotational step is brought about by causing the rotor of the motor 14 to be displaced angularly four times in succession to apply four rotational impulses to the table, the impulses being in two pairs with a short interval between each pair of impulses. The first impulse of the first pair is a short one and displaces the table in the desired direction of rotation. Owing to the inertia of the table, it overshoots the angular position which is compatible with the new angular position of the motor rotor, whereupon, by means of the pulley and belt arrangement (of which the belts are assumed to be inelastic), the motor rotor is forced to rotate beyond its new position. A restoring torque is at once developed in the stepping motor to return the rotor to its new position and this causes the table to start to oscillate about its rotational axis. The oscillation is reinforced by the second impulse of the pair which is applied to the table whilst the table is moving in the direction of application of the first impulse. Adjustment of the pulse sequence, in pulse magnitude and/or frequency, enables the dynamic response of the table to be adjusted. When the oscillation has died away substantially completely, the second pair of impulses are applied to the table which is again set in oscillation. When the second oscillation has died away, the table remains stationary until the end of the dwell period between steps.

The graphs shown in FIG. 3, in which values of distance are plotted as ordinates and values of time are plotted as abscissae, illustrates the manner in which the position of a vial as measured about the periphery of the table from a fixed position, for example the dispensing means, varies with time, and shows in particular the decay of oscillation after each pair of impulses and that after an oscillation the vial comes to rest at a new position. Trigger pulses used to trigger generation of the impulses are indicated in FIG. 3 at $a,b,c$ and $d$.

The oscillation is brought about in order to agitate the liquids in the vials and thereby mix the blood and reagents.

In another application, the apparatus is used in conjunction with a haematological analyser and comprises a turntable similar to the one described above, into which vials containing whole blood are fitted. In operation, each vial in turn is presented to a sampling mechanism comprising a syringe arrangement which is lowered into the vial so that a sample of whole blood may be removed from the vial and transferred to the haematological analyser for investigation. The oscillatory stepping of the turntable agitates the blood in the vials to ensure homogeneity of the blood at the time of sampling. Because of the extended cycle time of the analyser, the stepping may take the form of two forward steps in one sense and one backward step in the opposite sense. In this application, the rotatable arm and associated optical system are not required and so the shaft 5 may be solid.

The frequency of the oscillation is dependent upon the moment of inertia of the table, the torque displacement characteristic of the stepping motor, the input to output speed ratio of the drive between the stepping motor and the turntable, and the "stiffness" (i.e. ordinary and viscous friction) of the various bearing surfaces and in order to provide good mixing the width of a vial in the peripheral direction of the table should lie within certain limits with regard to the amplitude and frequency of the oscillation. If the frequency of oscillation is too high and/or the amplitude too low for the width of the vial, the oscillation might not bring about adequate mixing of the liquid in the vial, whereas if the frequency is too low and/or the amplitude is too high, the liquid might tend to be agitated to such an extent that it spills from the vial. The distance by which the vials move for each rotational step of the table and the velocity with which the vials move, depend upon the number of pulses applied to the motor, the angular displacement of the motor for each applied pulse (for example 1/200 revolution), and the reduction ratio between the motor and the turntable.

The moment of inertia of the table of the illustrated machine is considerably less than that of the table of the machine illustrated in Great Britain Patent application Nos. 51988/73 and 46608/74, the reduction having been achieved by reducing the mass of the table, this in turn being achieved by making the table in skeleton form, eliminating unnecessary material.

Although the illustrated machine is used for analysing blood, similar principles may be employed to provide machines for analysing other liquid specimens such as body liquids other than blood specimens. Generally speaking, the liquid specimen will comprise a single liquid or a sample of specimen material and additional material to be mixed therewith, the specimen material or the additional material being liquid and the other material not being gas.

We claim:

1. Specimen agitation apparatus comprising a substantially horizontal turntable having a relatively high moment of inertia and mounted to rotate about an upright central axis and formed to carry in fixed relation thereto in use, at respective positions substantially equally spaced from the said central axis and distributed substantially uniformly about the said central axis, a plurality of vessels for receiving liquid specimens to be agitated, and stepping drive means connected by means of a belt to the turntable to bring about stepwise rotation thereof about the said central axis, the stepping drive means being arranged to apply driving impulses to the turntable to bring about rotation thereof, and the stepping drive means and the turntable being so arranged that when the turntable is in a first rotational position about the said central axis and a driving impulse is applied to the turntable by the stepping drive means the turntable rotates to a second rotational position about the said central axis whereby the inertia of said turntable and the belt cause said turntable, before coming to rest at the second rotational position, to oscillate about the said central axis and thereby agitate specimens in vessels carried by the turntable.

2. Apparatus according to claim 1, wherein the arrangement of the stepping drive means and the turntable is such that the driving impulses are applied to the turntable in pairs such that the first impulse of the pair initiates oscillation of the turntable about the said central axis and the second impulse reinforces the oscillation, whereafter the turntable comes to rest.

3. Apparatus according to claim 2, wherein the arrangement of the stepping drive means and the turntable is such that all the steps are in the same sense.

4. Apparatus according to claim 2, wherein the arrangement of the stepping drive means and the turntable is such that the steps comprise, in succession, two steps in one sense and one step in the opposite sense.

5. Apparatus according to claim 2, further comprising dispensing means mounted adjacent the turntable at a predetermined location, the stepping drive means being arranged to bring each such vessel in turn to the said predetermined location so that the dispensing means can provide a liquid specimen in the said vessel.

6. Apparatus according to claim 2, wherein the arrangement of the stepping drive means and the turntable is such that each rotational step is brought about by applying two pairs of impulses to the turntable.

7. Apparatus according to claim 6, further comprising dispensing means mounted adjacent the turntable at a predetermined location, the stepping drive means being arranged to bring each such vessel in turn to the said predetermined location so that the dispensing means can provide a liquid specimen in the said vessel.

8. Apparatus according to claim 1, wherein the arrangement of the stepping drive means and the turntable is such that all the steps are in the same sense.

9. Apparatus according to claim 1, wherein the arrangement of the stepping drive means and the turntable is such that the steps comprise, in succession, two steps in one sense and one step in the opposite sense.

10. Apparatus according to claim 1, further comprising dispensing means mounted adjacent the turntable at a predetermined location, the stepping drive means being arranged to bring each such vessel in turn to the said predetermined location so that the dispensing means can provide a liquid specimen in the said vessel.

* * * * *